(12) United States Patent
Legallois et al.

(10) Patent No.: US 9,468,470 B2
(45) Date of Patent: Oct. 18, 2016

(54) ANCHOR FOR ATTACHMENT TO A BONY STRUCTURE

(71) Applicant: Zimmer Spine, Bordeaux (FR)

(72) Inventors: Georges Legallois, Bordeaux (FR); Gilles Larroque-Lahitette, Baron (FR)

(73) Assignee: Zimmer Spine (FR)

( * ) Notice: Subject to any disclaimer, the term of this patent is extended or adjusted under 35 U.S.C. 154(b) by 0 days.

(21) Appl. No.: 14/589,297

(22) Filed: Jan. 5, 2015

(65) Prior Publication Data

US 2015/0112391 A1 Apr. 23, 2015

Related U.S. Application Data

(63) Continuation of application No. PCT/EP2013/064438, filed on Jul. 9, 2013.

(30) Foreign Application Priority Data

Jul. 9, 2012 (EP) .................................... 12305819

(51) Int. Cl.
*A61B 17/70* (2006.01)

(52) U.S. Cl.
CPC ....... *A61B 17/7032* (2013.01); *A61B 17/7056* (2013.01); *A61B 17/7076* (2013.01)

(58) Field of Classification Search
CPC ...................... A61B 17/7047; A61B 17/7056; A61B 17/7032; A61B 17/7034
USPC ................................ 606/276, 277, 324, 330
See application file for complete search history.

(56) References Cited

U.S. PATENT DOCUMENTS

| | | | |
|---|---|---|---|
| 5,010,879 A | 4/1991 | Moriya et al. | |
| 5,147,359 A | 9/1992 | Cozad et al. | |
| 5,181,917 A | 1/1993 | Rogozinski | |
| 5,346,493 A | 9/1994 | Stahurski et al. | |
| 5,507,747 A * | 4/1996 | Yuan ................... | A61B 17/7043 24/514 |
| 6,547,789 B1 | 4/2003 | Ventre et al. | |
| 7,901,436 B2 | 3/2011 | Baccelli | |
| 2003/0130659 A1* | 7/2003 | Haider ............... | A61B 17/7032 606/302 |
| 2007/0016189 A1 | 1/2007 | Lake et al. | |
| 2007/0083199 A1* | 4/2007 | Baccelli ............. | A61B 17/7032 606/273 |
| 2007/0161990 A1 | 7/2007 | Hillyard et al. | |
| 2008/0086131 A1* | 4/2008 | Daly .................. | A61B 17/7032 606/264 |
| 2008/0234744 A1* | 9/2008 | Zylber ............... | A61B 17/7005 606/264 |
| 2011/0152950 A1 | 6/2011 | Baccelli | |

FOREIGN PATENT DOCUMENTS

WO 2005023126 A1 3/2005

* cited by examiner

*Primary Examiner* — Eduardo C Robert
*Assistant Examiner* — Julianna N Harvey
(74) *Attorney, Agent, or Firm* — Schwegman Lundberg & Woessner, P.A.

(57) ABSTRACT

Anchor for attachment to a bony structure, comprising a hook, an anchor body with a distal wall facing the hook, and a fastening system for fastening a connection member to the anchor body. A slot is defined between the hook and the distal wall, for receiving a bony structure such as a vertebra portion. The anchor further comprises a retention member having a distal end with teeth, passing through the distal wall and being movable relative to the anchor body, from a retracted position to a protracted position where the distal end protrudes from the distal wall, inside the slot. The proximal end of the retention member defines a seat for the connection member.

14 Claims, 5 Drawing Sheets

ANCHOR FOR ATTACHMENT TO A BONY STRUCTURE

CROSS-REFERENCE TO RELATED APPLICATIONS

The present application is a continuation application of International Application PCT/EP2013/064438, filed Jul. 9, 2013, which claims priority to European Application No. 12305819.0 filed Jul. 9, 2012 the complete disclosures of which are herein incorporated by reference.

FIELD OF THE INVENTION

The present disclosure relates to an anchor for attachment to a bony structure, to a stabilization system comprising such an anchor and to a method using it. This anchor may be helpful for holding a bone (e.g. a vertebra) and a connection member (e.g. a rod) in a desired configuration. In particular, the present disclosure relates to a system and method for stabilizing at least two vertebrae.

BACKGROUND OF THE INVENTION

One field of application for the invention is holding together a bone and a connection member in a desired relative position (while allowing in some cases a limited amount of relative movement), for example to aid in healing of breaks or to correct bony structure deficiencies and abnormalities. In particular, sufferers of abnormal spine curvature, spine deficiencies or other spine abnormalities (including scoliosis, instability of spinal segments or degenerated intervertebral discs) may benefit from the invention.

The spine is formed of superposed vertebrae, normally aligned along a vertebral axis, from the lumbar vertebrae to the cervical vertebrae, each having an anterior part: the vertebral body, and a posterior part: the vertebral arch (or neural arch). The anterior and posterior parts enclose the vertebral foramen. Each vertebral arch is formed by a pair of pedicles and a pair of laminae, with transverse processes and/or a spinous process (or neural spine) projecting therefrom. The transverse processes and the spinous process project opposite to the vertebral foramen.

When the vertebrae are articulated with each other, the vertebral bodies form a strong pillar for the support of the head and trunk. In between every pair of vertebral bodies, there is an intervertebral disc.

When the spine of a person has abnormal curvature (e.g. scoliosis) or other deficiencies (e.g. a damaged intervertebral disc), the vertebrae are typically too close together, too far apart or otherwise misaligned, and there is a need to stabilize the vertebrae in a correct position relative to one another. Mainly, there is either a need to compress the vertebrae (i.e. to bring and hold them closer together) or a need to distract the vertebrae (i.e. to move and keep them away from each other).

Typically, known stabilization devices include at least two anchors configured to be fastened, respectively, to two vertebrae, and a rod or other elongate member for connecting the anchors together, thereby providing stabilization between the vertebrae.

In one kind of device, known in the art, said anchors comprise a hook that rests on the vertebrae. Examples of such devices are disclosed, for instance, in PCT Application Publication No. 2005/023126, U.S. Pat. No. 4,269,178, U.S. Pat. No. 6,740,089, or US Application Publication No. 2007/0161990.

Compared to a pedicle screw, a hook has the advantage of providing a rigid and strong anchoring to the vertebra, but the physician (or other operative) may have difficulty in placing the hook correctly on the vertebra. Indeed, the position of the hook on the vertebra is unstable (i.e. the hook may slip out of place) until the rod or other elongate member is positioned and connected to all the anchors. Moreover, it is possible in some systems that the hook may disengage from the vertebra. Accordingly, the physician may decide to use more hook anchors than necessary in a spinal stabilization construct.

While known devices have proven effective, further improvements would be beneficial.

SUMMARY OF THE INVENTION

Described is an anchor for attachment to a bony structure. This anchor comprises: a hook, an anchor body and a fastening system for fastening a connection member to the anchor body. In an exemplary anchor, the anchor body has a proximal side, a distal side, a distal wall facing the hook, and a first passage. The first passage extends through the distal wall, in the proximal-distal direction, between a proximal opening and a distal opening. A slot is defined between the hook and the distal wall, the slot being configured to receive a bony structure (e.g. a vertebra portion) and the hook being configured to rest on the bony structure, The anchor further comprises a retention member having a proximal end and a distal end. The retention member is received in the first passage and is movable relative to the anchor body, in the proximal-distal direction, from a retracted position where the proximal end of the retention member protrudes out of the proximal opening of the first passage, to a protracted position where the distal end protrudes out of the distal opening of the first passage, inside the slot.

A push force can be exerted on the proximal end to move the retention member towards the hook (i.e. from its refracted position to its protracted position). As a result, when the anchor is in place on a bony structure and when the retention member is pushed towards the hook, its distal end protrudes inside the slot and engages the bony structure. Such engagement may be obtained by pressing the retention member against the bony structure in order to provide a desired holding force and/or by making the distal end penetrate into the bony structure. Thereby, the hook is better fastened on the bony structure—i.e. the stability of the hook on the bony structure is improved. Moreover, the risk that the hook may disengage from the bony structure is lowered since the retention member provides additional engagement with the bony structure. The attachment to the bony structure is, therefore, more reliable.

In addition, the hook provides a rigid and strong connection to the bony structure while preventing fatigue phenomena in the connection over time.

In an exemplary anchor, the proximal end of the retention member defines a seat for the connection member. In other terms, the proximal end of the retention member is so shaped that the connection member fits on the proximal end, and stable engagement is obtained between the retention member and the connection member. As a result, relative micromotions between those two members are avoided (or at least limited). Further, stresses between those two members are evenly distributed on the contact interface defined by the seat, and highly localized stress concentrations are avoided (or at least limited) in the connection member. In addition, when the connection member fits in the seat, the possible rotation movement of the retention member about the distal-proximal direction is impeded. Thus, stable engagement is obtained between the retention member and the bony structure.

The seat may be formed by a groove extending essentially transverse to the proximal-distal direction and having, in cross-section, a concave profile, in particular a part-circular, U-shaped, wedge-shaped or V-shaped profile. Any profile that can substantially complement the external profile of the connection member can be used.

The distal end of the retention member may comprise a flat surface for engaging with the vertebrae, which surface may be roughened, scored, knurled, or otherwise modified to improve engagement with the bony structure. The distal end may also comprise tapered, rounded, bullet-nosed, pyramidal, wedge, knife-edge, or serrated shapes and/or structures. Any structure that can provide at least some frictional resistance between the distal end and the surface of a bone can be used.

In certain embodiments, the distal end of the retention member defines at least one protruding element for engagement with the bony structure. The protruding element may have any desired structure or shape that can positively engage with the bony structure. For example, the protruding element may be tapered so as to penetrate into the bony structure. The protruding element may be a spike.

In certain embodiments, the distal end of the retention member is crown-shaped, so as to improve engagement with the bony structure. For instance, the distal end may comprise a circular arrangement of protruding elements on its distal edge. More particularly, the distal end may have a serrated circular edge.

To better transmit the push force from one side of the distal wall to the other, the retention member may be rigid (i.e. inflexible or hardly flexible) at least in the proximal-distal direction.

In certain embodiments, the retention member is freely movable in the distal-proximal direction relative to the anchor body, thereby avoiding helical motion or screwing motion between the retention member and the anchor body. More especially, a play or gap may exist between the retention member and the inner surface of the first passage, and the outer surface of the retention member and the inner surface of the first passage may be substantially smooth. In particular, these surfaces may be free of threads or analogous circumferential structures. Free translation movement of the retention member in the distal-proximal direction allows, notably, a better transmission of the push force.

In certain embodiments, the anchor body is provided with a main passage extending essentially transverse to the proximal-distal direction and being configured to receive a portion of the connection member, and the proximal end of the retention member protrudes inside the main passage in the protracted position, when no push force is exerted on the retention member. Accordingly, when the connection member (or another element) is inserted into the main passage, a push force is exerted on the proximal end by the connection member (or the other element), thereby moving the retention member towards the hook (i.e. to the protracted position).

In certain embodiments, the system for fastening the connection member comprises a locking member for engagement with the anchor body, the locking member engaging with the anchor body and being displaceable so as to push the portion of the connection member towards the hook, thereby clamping the connection member inside the main passage. At the same time, the connection member may push on the proximal end of the retention member, thereby making the distal end engage the bony structure. The locking member may be located opposite the hook with respect to the distal wall, which makes the locking member easier to access for the physician.

Of course, other fastening systems might be used for fastening the connection member to the anchor body, including for instance clamping or mating systems with frictional or mechanical engagement, for example flanges and/or cam surfaces.

In certain embodiments, the anchor body is provided with an open cavity extending essentially in the proximal-distal direction (away from the hook) and opening out on the proximal side of the anchor body. The open cavity has a bottom which is defined, at least in part, by the proximal end of the retention member.

The open cavity may be a substantially U-shaped channel defined by two lateral walls extending proximally from the bottom of the cavity. With such a configuration, the connection member may be side-loaded or top-loaded into the anchor body.

The anchor body may be provided with an engagement feature, such as a threaded part, around the open cavity. The locking member may be provided with a complementary engagement feature, such as a thread, for engagement with the engagement feature of the anchor body. In this case, once the connection member has been inserted into the open cavity, it is pushed towards the hook by screwing the locking member into the anchor body, or otherwise engages the engagement feature of the locking member with the engagement feature of the anchor body.

In certain embodiments, the retention member has a distal shank surmounted by a proximal enlarged head, and the first passage of the anchor body is configured to accommodate the shank. The head of the retention member has a cross-section larger than the cross-section of the first passage so that the head abuts against on the distal wall when the retention member is moved towards the hook. Thus, in the protracted position, the distal end cannot protrude inside the slot beyond a maximum distance. By limiting the protrusion distance, the risk of damaging the bony structure, when it is engaged by the distal end, is limited.

In certain embodiments, the hook is integral with the anchor body. This reduces the number of pieces in the anchor and provides a strong connection between the hook and the anchor body. In other embodiments, the hook may be formed as a separate component coupled to the anchor body.

The anchor may be a vertebral anchor, the above-mentioned bony structure being a vertebra.

Also described is a stabilization system comprising at least one anchor as described above and a connection member to be fastened to the anchor body.

The connection member may be rigid, semi-rigid, or flexible. For instance, the connection member may be a rod or other elongate member. It may also be a cord or a bushing.

As already explained, in such a system, the connection member may push the retention member towards the hook (i.e. towards the bony structure for engagement therewith) when it is fastened to the anchor body.

Also described is a stabilization system for stabilizing at least two bony structures, in particular two vertebrae. The system comprises a first anchor configured to be fixed to a first bony structure, and a second anchor configured to be fixed to a second bony structure, the first and second anchors being connectable together, through the connection member, for providing stabilization between the first and second bony structures. In such a stabilization system, at least the first anchor is an anchor as described above.

Such a stabilization system may be used for providing "static stabilization" or "dynamic stabilization" between the vertebrae. Static stabilization typically refers to holding together the vertebrae in a particular relative position, while minimizing movement between the vertebrae, whereas dynamic stabilization typically refers to holding together the vertebrae in a particular relative position, while allowing a limited amount of relative movement between the vertebrae. For dynamic stabilization, the connection member may have elastic properties.

Also described is a method for stabilizing at least two bony structures, in particular two vertebrae, comprising the steps of:
  providing a stabilization system as described above;
  impeding relative movement between the first anchor and a first bony structure by fixing the first anchor to the first bony structure,
  impeding relative movement between the second anchor and a second bony structure by fixing the second anchor to the second bony structure, and
  impeding relative movement between the first and second anchors by connecting the first and second anchors together, through the connection member.

The step of fixing the first anchor to the first bony structure may comprise the following sub-steps:
  pre-fixing the first anchor to the first bony structure by engaging at least partially the distal end of the retention member with the first bony structure, and
  subsequently, fastening the connection member to the first anchor with the fastening system.

Such a method is easy to implement and has advantages derived from the use of a stabilization system as described above.

The pre-fixing step may be performed by using a tool such as the one as described hereinafter or another tool adapted to exert a push force on the retention member.

The pre-fixing step provides the advantage of stabilizing the position of the first anchor on the bony structure before setting up the connection member. Thus, the handling of the system is made easier.

The stabilization system may be used for distracting the first and second bony structures or for compressing them, depending on the position of the anchor slots relative to the bony structures.

Also described is a tool for pre-fixing an anchor as described above, to a bony structure, the tool comprising an elongate body with a distal end and a sleeve movable along the elongate body until abutting on the distal end, and rotatable around the elongate body, the distal end being configured to be inserted into the open cavity of the anchor, and the sleeve being provided with a complementary engagement feature, such as a threaded end, for engagement with the engagement feature of the anchor. When the sleeve engages (e.g. when it is screwed into) the anchor body, the sleeve pushes on the distal end which, in turn, pushes on the retention member, thereby making the retention member engage the bony structure.

In certain embodiments, the sleeve is provided with a handle allowing the physician to easily move the sleeve in rotation and translation relative to the elongate body. This handle may be located opposite the threaded end.

The elongate body may also be provided with a handle allowing the physician to position the elongate body in the patient's body and, especially, to insert the distal end into the open cavity of the anchor-body. This handle may be located opposite the distal end.

In certain embodiments, the distal end is substantially T-shaped and comprises a bar extending substantially perpendicular to the elongate body. The bar is intended to be positioned in the main passage of the anchor body in place of the connection member. It may have a shape comparable or similar to the shape of the connection member, such as an elongate shape with a convex or rounded profile. When the sleeve is screwed into the anchor, or otherwise engaged with the anchor, the bar pushes the retention member towards the hook.

In certain embodiments, the bar is provided with a protrusion forming an abutment. The protrusion is intended to abut on the anchor body when the distal end is positioned in the main passage, thereby impeding movement of the bar relative to the anchor in the bar axis direction. The protrusion thus facilitating the positioning of the distal end relative to the anchor body.

Other features and advantages of the invention will become apparent from the following detailed description, taken in conjunction with the accompanying drawings, which illustrate, by way of example, some principles of the invention.

BRIEF DESCRIPTION OF THE DRAWINGS

In the drawings, like reference signs generally refer to the same parts throughout the different views. The drawings are not necessarily to scale, emphasis instead generally being placed upon illustrating the principles of the invention.

DETAILED DESCRIPTION

In the following detailed description, it is referred to the accompanying drawings showing an example of anchor, of stabilization system and an example of fixing tool. It is intended that these examples be considered as illustrative only, the scope of the invention not being limited to those examples.

The anchors and stabilization system are placed on vertebrae in the following example. However, such anchors and stabilization systems might be placed on other bony structures.

Figure 3:
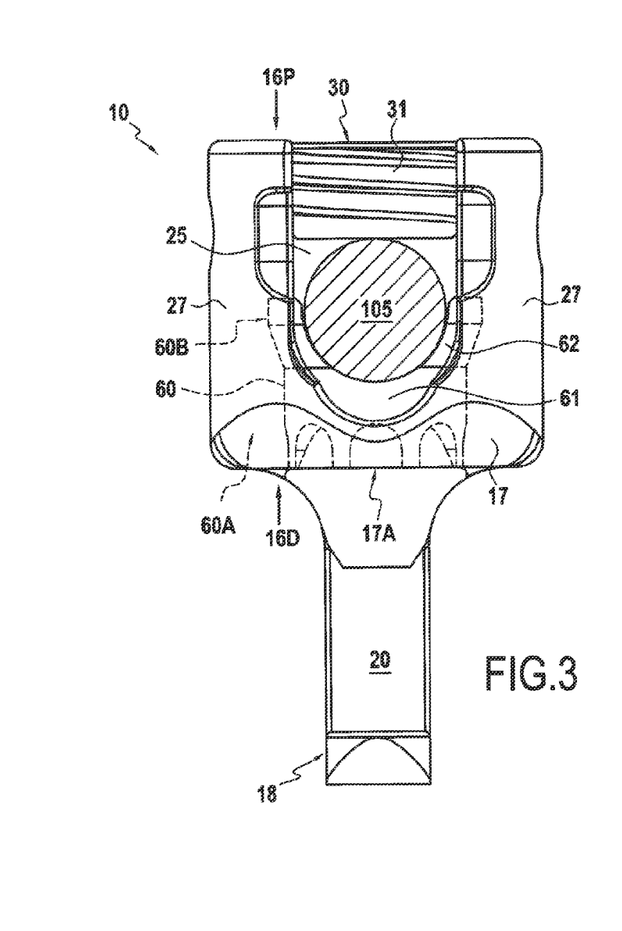
FIG. 3 is a front view (see arrow III) of the anchor of FIG. 2, the retention member of the anchor being in a retracted position.
Figure 4:
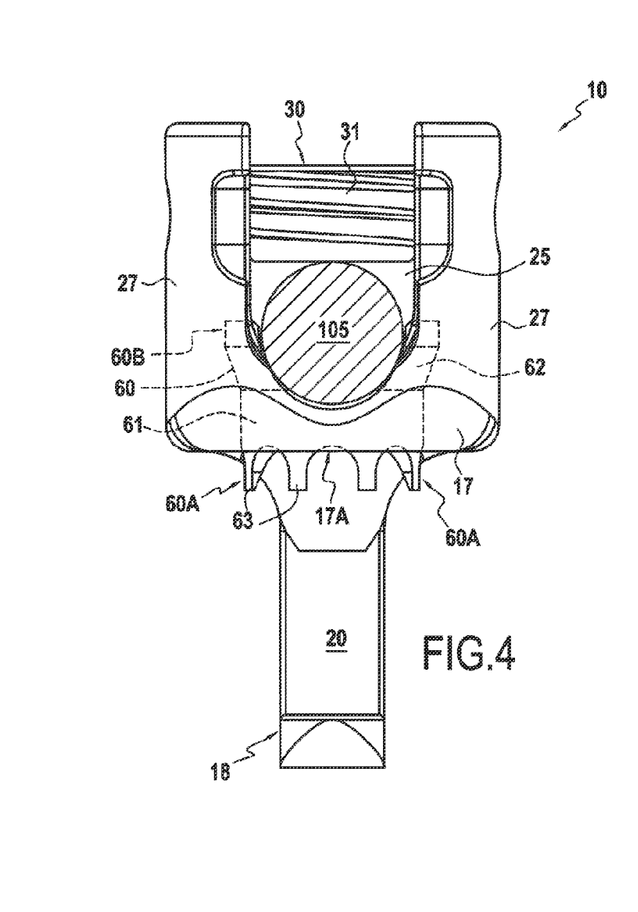
FIG. 4 is a front view like that of FIG. 3, where the retention member is in a protracted position.
Figure 5:
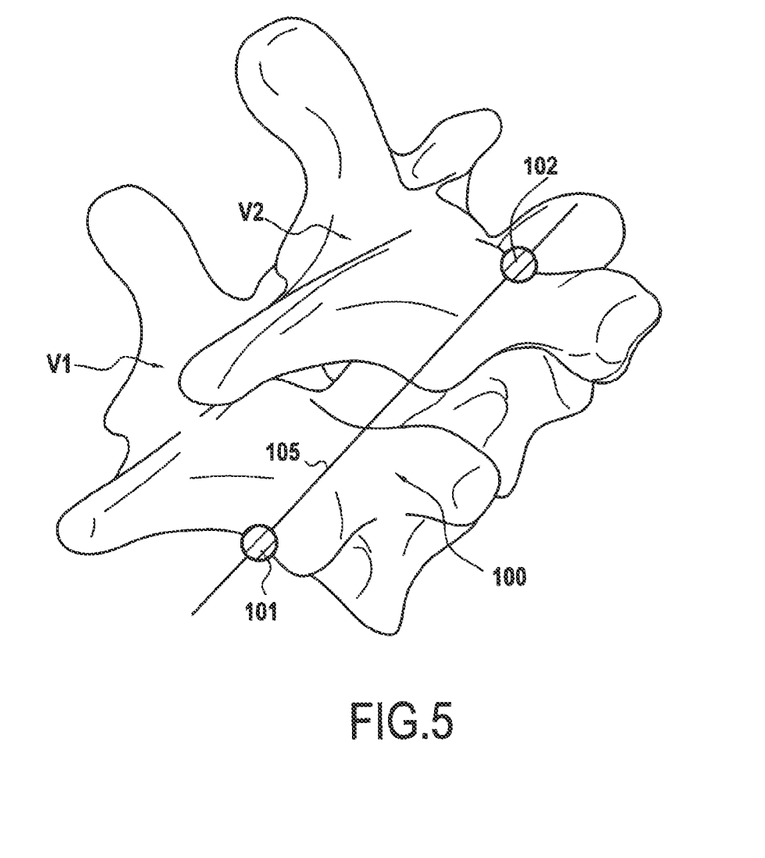
FIG. 5. is a diagrammatic view showing an example of a stabilization system in place on two vertebrae.

An example of an anchor 10 for attachment to a vertebra VI is shown in FIGS. 1 to 4, while an example of a stabilization system 100 for stabilizing at least two vertebrae VI, V2 (i.e. for holding together these two vertebrae in a particular relative position) is shown in FIG. 5.

Stabilization system 100 comprises:
a first anchor 101 adapted to be fixed to a first vertebra VI,
a second anchor 102 adapted to be fixed to a second vertebra V2, and
a connection member for connecting the first and second anchors 101, 102 together, thereby providing stabilization between the first and second vertebrae VI, V2.

Here, the connection member is a rod 105 that, for instance, may be rigid and made of biocompatible metallic material. In other embodiments (not shown), the connection member may be semi-rigid or flexible, and may be made of a biocompatible metallic material or biocompatible polymer material, for example.

At least the first anchor 101 is an anchor 10 as shown in FIGS. 1 to 4. The first and second anchors 101, 102 may be the same or different. If different, the second anchor 102 may be, for instance, of screw type or flexible-tie type. In the example shown, however, the first and second anchors 101, 102 are like the anchor 10 and are respectively fastened to the laminae of vertebrae VI, V2.

Turning now to FIGS. 1 to 4, the anchor 10 comprises: an anchor body 16, a hook 18 that is integral with the anchor body 16, a retention member 60, and a locking member 30.

The anchor body 16 has a proximal side 16P, a distal side 16D, a central axis C extending in the proximal-distal direction, and a distal wall 17, or bottom wall, substantially perpendicular to the proximal-distal direction. The distal wall 17 has opposite first and second faces 17A, 17B, the first face 17A facing the hook 18.

The hook 18 extends from the distal wall 17. The hook 18 extends from one point on the periphery of the first face 17A (in the proximal-distal direction) and curves round in a diametrically opposed direction, the free end of the hook 18 becoming substantially parallel to the first face 17A. However, the hook 18 might have a different shape.

A slot 20 is defined below the anchor body 16, by the internal face 18A of the hook 18 and the first face 17A of the distal wall 17. The shape and size of the slot 20 are such that a bony portion of the first vertebra VI (e.g. a lamina of vertebra VI—shown in dotted line in FIG. 2) can be inserted into the slot 20.

The anchor body 16 is provided with a channel 25 delimited by the distal wall 17 and two lateral walls 27 extending from the distal wall 17 in the direction opposite to the hook 18, i.e. upwards in FIGS. 1-4. The channel 25 opens out on the proximal side 16P of the anchor body. It also opens out laterally on opposite lateral sides 16S of the anchor body. In cross-section, the channel 25 is substantially U-shaped. Thus, the channel 25 defines a groove on the proximal side 16P the anchor body 16, which extends from one lateral side 16S to the other.

The channel 25 defines a main passage 25A for receiving a portion of the rod 105, the main passage 25A extending substantially parallel to the rod axis R and perpendicular to the central axis C. The channel 25 also defines an open cavity 25B extending above the main passage 25A, substantially parallel to the central axis C and perpendicular to the rod axis R. The main passage 25A and the open cavity 25B meet above the distal wall 17.

The anchor body 16 is further provided with a first passage 24 going through the distal wall 17 and opening out in the slot 20, in front of the hook 18, thereby defining a distal opening 24D. The first passage 24 extends parallel to the central axis C (i.e. in the proximal-distal direction) and communicates with the channel 25, through a proximal opening 24P. First passage 24 is located below the channel 25 (i.e. below the main passage 25A). In this example, first passage 24 and open cavity 25B are substantially aligned along central axis C.

Anchor 10 also comprises a locking member 30 (illustrated in FIGS. 2-4 but not in FIG. 1) for engagement with the anchor body 16. Here, the locking member 30 is a set screw provided with an external thread 31 for rotary engagement with a threaded part 13 provided on the inside of the anchor body 16, on the upper part of the U-shaped cavity 25 (i.e. around the open cavity 25B). Alternatively, the locking member 30 may be provided with an inside thread for rotary engagement with a threaded part provided on the outside of the anchor body 16. In other embodiments, the locking member 30 may include other engagement features configured to mate with complementary engagement features of the anchor body 16.

Thus, the rod 105 may be clamped between the locking member 30 and the anchor body 16 by moving the locking member 30 relative to the anchor body 16.

The locking member 30 is located opposite the hook 18 with respect to the main passage 25A, which makes the locking member 30 accessible and easy to operate when the hook 18 is placed on a vertebra.

The anchor 10 also comprises a retention member 60 with opposite distal and proximal ends 60A, 60B. The retention member 60 has a distal shank 61 surmounted by an enlarged head 62. The retention member 60 goes through the distal wall 17, via the first passage 24. More precisely, the distal shank 61 goes through the first passage 24 whereas the head 62, which has a cross-section which is larger than the cross-section of the first passage 24, abuts against the distal wall 17 when the retention member 60 is moved towards the hook 18, i.e. downwards in the FIGS. 1-4.

In this example, the retention-member distal shank 61 is tubular shaped and has a serrated circular edge defining teeth 63 positioned around the circumference. Teeth 63 may be configured to penetrate into the vertebra VI (see FIG. 2).

Figure 1:
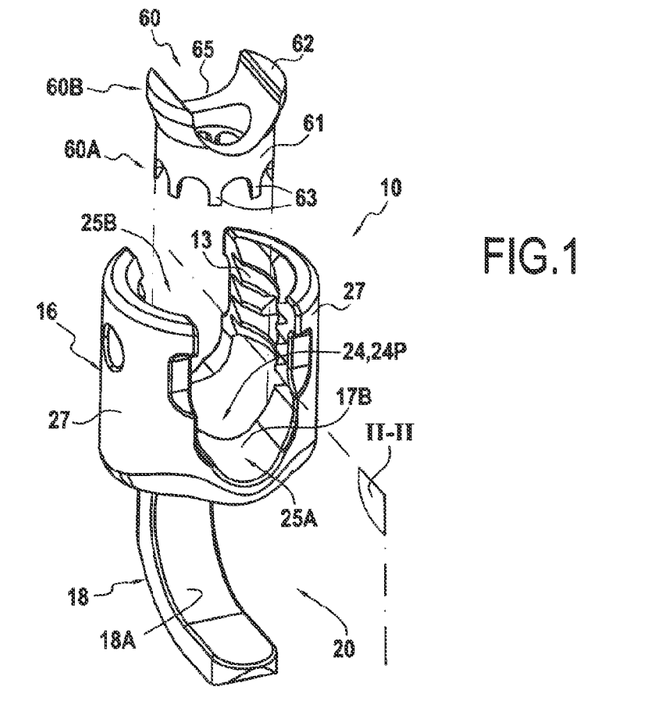
FIG. 1 is an exploded perspective view of an example of an anchor.
Figure 2:
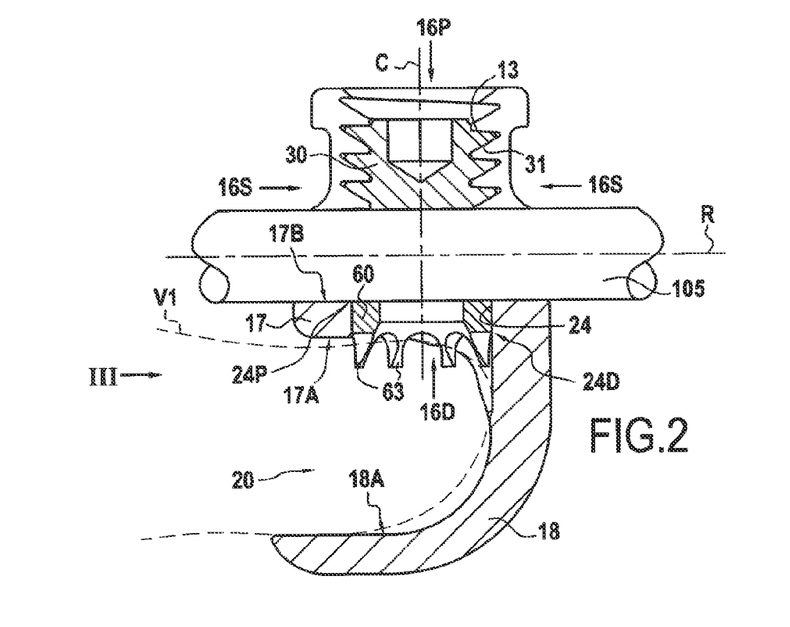
FIG. 2 is sectional view (along plane II-II) of the anchor of FIG. 1 with a connection member fastened thereto.

The retention-member head 62 has a larger diameter than the diameter of the distal shank 61 and defines a seat 65 on its top surface (see FIG. 1) for receiving the rod 105. The seat 65 is formed by a groove extending diametrically and having, in cross-section, a concave profile substantially corresponding to the external profile of the rod 105 (see FIGS. 3-4). Thus, the rod 105 fits correctly in the seat 65 and full engagement is obtained between the retention member 60 and the rod 105, as illustrated in FIGS. 2-4. With this engagement, the rotation movement of the retention member 60 about axis C is impeded and, thus, relative rotary movement between the retention member 60 and the vertebra VI is impeded.

The retention member 60 may be pre-assembled with the anchor body 16.

The retention member 60 is movable relative to the anchor body 16 from a first position, or retracted position, to a second position, or protracted position. In the retracted position, shown in FIG. 3, the proximal end 60B of the retention member protrudes inside the main passage 25A while the distal end 60A fits flush into the first passage 24 (i.e. when the distal end 60A is flush with the distal opening 24D). In the protracted position, shown in FIG. 4, the proximal end 60B is pushed down while the distal end 60A and especially the teeth 63 protrude from the first face 17A, inside the slot 20. In the protracted position, the retention-member head 62 abuts on the second face 17B of the distal wall 17, to limit the depth that the teeth 63 protrude into the slot 20 and thus into the bony structure positioned in the slot 20.

The retention member 60 is moved from the retracted position to the protracted position by exerting a push force on the proximal end 60B. The push force may be exerted by the rod 105 or a tool 200 (as explained further). As a result, when the anchor 10 is positioned on a vertebra VI and when the retention member 60 is pushed towards the hook 18, into its protracted position, the distal end 60A, such as the teeth 63 engage the vertebra VI, thereby improving the attachment thereto. The interaction of the hook 18 and retention member 60 thus provides securement for the anchor 10, in which the stability provided by the retention member 60 strengthens and enhances the hook attachment, and wherein the hook 18 prevents fatigue phenomena over time.

To avoid damaging the vertebra VI, the push force exerted on the proximal end 60B may be controlled and/or limited, e.g. with a system for controlling and/or limiting the maximum torque exerted on the locking member 30. In such cases, if the vertebra VI resists against the push force (e.g. because of its hardness), the distal end 60A may not fully engage the vertebra VI and the retention member 60 may not reach its full protracted position but, instead, may reach an intermediate position (between the positions of FIGS. 3 and 4) where the proximal end 60B is not fully pushed down. In this intermediate position, because the rod 105 fits in the seat 65, the contact area between these two parts is not limited to a single point or line, which allows relative micromotions between the rod 105 and the retention member 60 to be avoided (or at least limited). Thus, stability is obtained, even in an intermediate position. Further, since stresses generated by the push force are evenly distributed on the contact interface defined by the seat 65, highly localized stress concentrations in the rod 105 are avoided (or at least limited).

Figure 6:
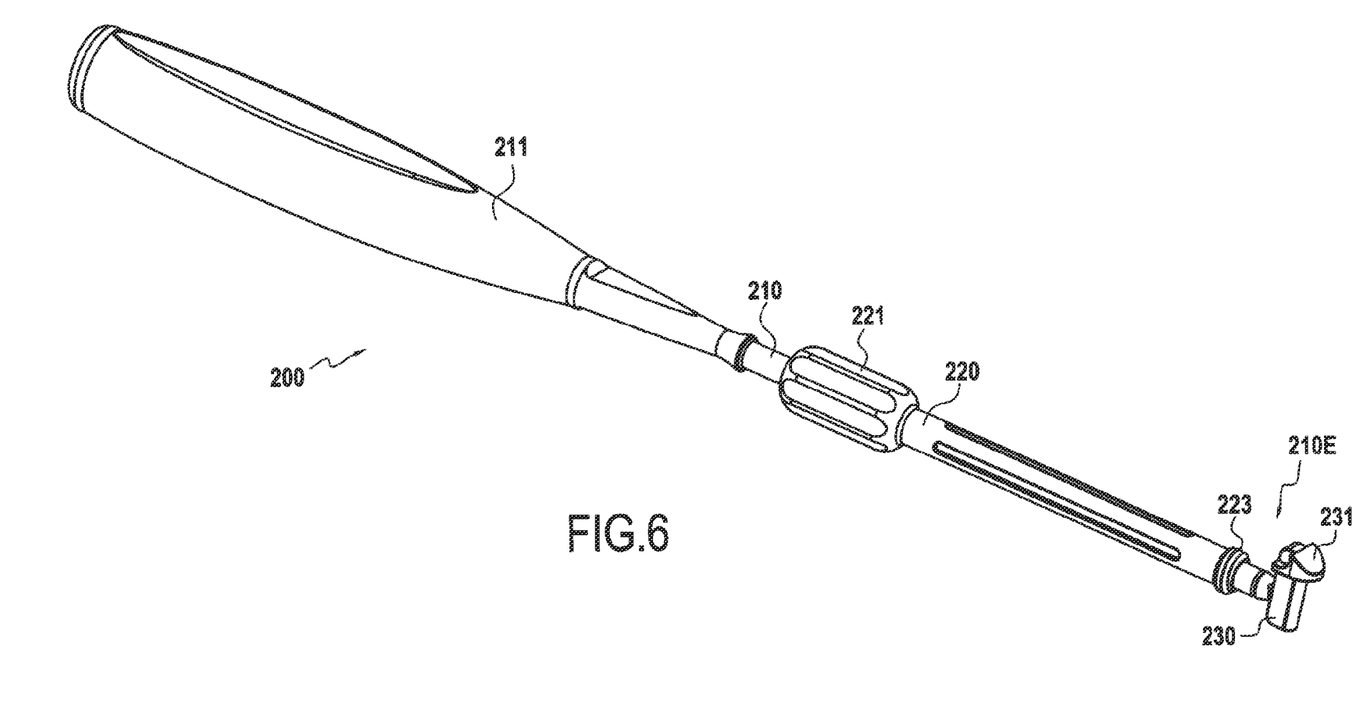
FIG. 6 is a perspective view of an example of a tool for pre-fixing an anchor.
Figure 7:
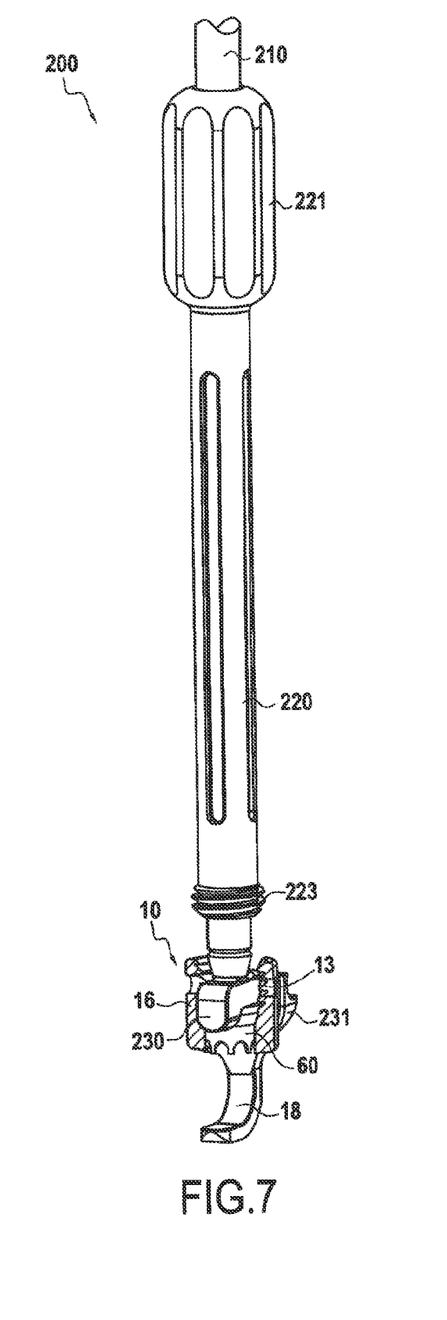
FIG. 7 is a view showing the tool of FIG. 6 in cooperation with the anchor of FIG. 1, the retention member of the anchor being in a retracted position.
Figure 8:
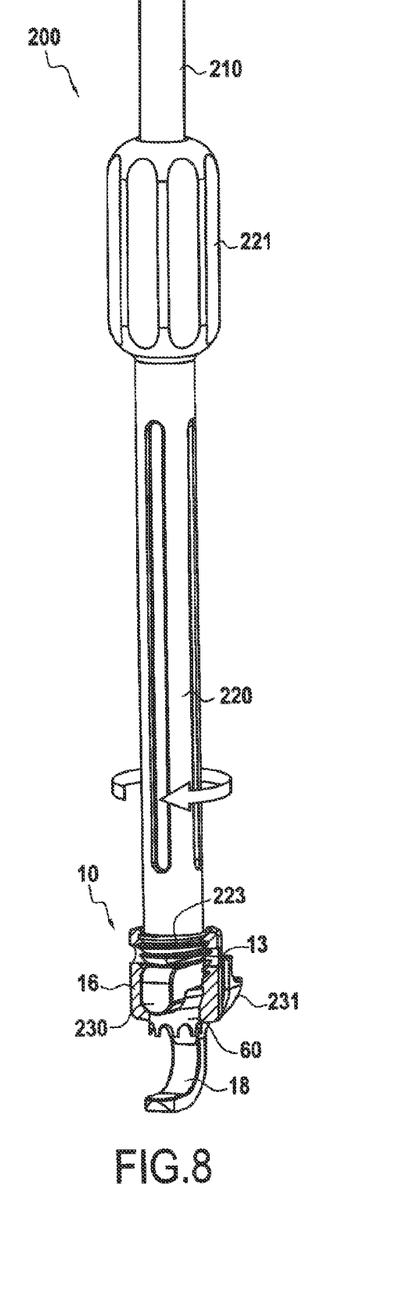
FIG. 8 is a view like that of FIG. 7, where the retention member is in a protracted position.

FIGS. 6 to 8 show a tool 200 for pre-fixing an anchor 10 such as the one of FIGS. 1 to 4, to a bony structure (e.g. a vertebra).

The tool 200 comprises an elongate body 210 (e.g. a metal rod) with a distal end 210E and a sleeve 220 movable along the elongate body 210 until abutting on the distal end 210E. The sleeve 220 is also rotatable around the elongate body 210. Opposite the distal end 210E, the elongate body 210 comprises a handle 211 for holding and positioning the elongate body 210 during surgery.

The distal end 210E is configured to be inserted into the open cavity 25B of the anchor 10 as shown in FIGS. 7 and 8 (the anchor 10 being shown in cutaway view in those figures). More precisely, the distal end 210E is substantially T-shaped and comprises a bar 230 connected at the end of the elongate body 210 and extending substantially perpendicular to the elongate body 210 (see FIG. 6). The bar 230 is configured to be inserted into the main passage 25B of the anchor 10, as shown in FIGS. 7 and 8. When inserted in the main passage 25B, the bar extends perpendicular to the proximal-distal direction of the anchor, while the elongate body 210 extends parallel to the proximal-distal direction and, in the example, along axis C.

The bar 230 is provided, at one end, with a protrusion 231 forming an abutment, e.g. a shoulder or flange. The protrusion 231 helps the physician to correctly position the bar 230 relative to the anchor 10: when the protrusion 231 abuts on the lateral face of the anchor body 16, the bar 230 is well positioned in the main passage 25B. The protrusion 231 also prevents the bar 230 from sliding out of the main passage 25B.

The sleeve 220 is provided with a threaded end 223 for rotary engagement with the threaded part 13 of the anchor 10 and with a handle 221 allowing the physician (or other operative) to translate and rotate the sleeve 220 and, therefore, to screw it into the anchor 10.

The tool 200 is operated as follows. Once the bar 230 is well positioned in the anchor 10, the sleeve 220 is screwed into the anchor 10, the threaded end 223 pushing on the bar 230 which, in turn, pushes on the retention member 60 which engages the bony structure. As a result, the anchor 10 is pre-fixed to the bony structure. Then, the tool 200 is removed before setting up the rod 105.

The above description is given by way of example, and not limitation. Given the above disclosure, one skilled in the art could devise variations that are within the scope of the invention. Further, the features of the embodiments or examples disclosed herein can be used alone or in varying combinations with each other, and are not intended to be limited to the specific combination described herein.

What is claimed is:

1. An anchor for attachment to a bony structure, the anchor comprising:
   a hook;
   an anchor body, the anchor body having a proximal side, a distal side, a central longitudinal axis, a distal wall facing the hook, and a first passage extending along the central longitudinal axis through the distal wall between a proximal opening and a distal opening in a proximal-distal direction;
   a fastening system for fastening a connection member to the anchor body;
   a slot defined between the hook and the distal wall, the slot being configured to receive a bony structure and the hook being configured to rest on the bony structure; and
   a retention member having a proximal end and a distal end, the proximal end of the retention member defining a seat for the connection member, the retention member being received in the first passage and movable relative to the anchor body, in the proximal-distal direction along the central longitudinal axis, from a retracted position where the proximal end of the retention member protrudes out of the proximal opening of the first passage, to a protracted position where the distal end protrudes out of the distal opening of the first passage and into the slot, wherein the distal end of the retention member includes an integrated serrated circular edge defining teeth positioned around the circumference forming a crown-shape, and wherein the retention member includes a distal shank surmounted by a proximal enlarged head, and wherein the first passage has a cross-section configured to accommodate the shank, the head having a cross-section being larger than the cross-section of the first passage so that the head abuts on the distal wall when the retention member is moved towards the hook.

2. The anchor of claim 1, wherein the seat is formed by a groove extending essentially transverse to the proximal-distal direction and having, in cross-section, a concave profile.

3. The anchor of claim 2, wherein the concave profile is a U-shaped profile.

4. The anchor of claim 1, wherein the anchor body includes a main passage extending essentially transverse to the proximal-distal direction and configured to receive a portion of the connection member, and wherein the proximal end of the retention member protrudes into the main passage in the protracted position.

5. The anchor of claim 4, wherein the fastening system includes a locking member for engagement with the anchor body, the locking member engaging with the anchor body and being displaceable so as to push the portion of the connection member towards the hook, thereby clamping the connection member inside the main passage.

6. The anchor of claim 1, wherein the retention member is rigid in the proximal-distal direction.

7. The anchor of claim 1, wherein the retention member is freely movable in the distal-proximal direction relative to the anchor body.

8. The anchor of claim 1, wherein the anchor body includes an open cavity extending essentially in the proximal-distal direction and opening out on the proximal side of the anchor body, wherein the open cavity has a bottom which is defined, at least in part, by the proximal end of the retention member, and wherein the anchor body includes an engagement feature around the open cavity.

9. The anchor of claim 8, wherein the engagement feature is a threaded part.

10. A stabilization system comprising:
   an anchor including:
      a hook;
      an anchor body, the anchor body having a proximal side, a distal side, a central longitudinal axis, a distal wall facing the hook, and a first passage extending through the distal wall between a proximal opening and a distal opening in a proximal-distal direction along the central longitudinal axis;
      a fastening system for fastening a connection member to the anchor body;
      a slot defined between the hook and the distal wall, the slot being configured to receive a bony structure and the hook being configured to rest on the bony structure; and
      a retention member having a proximal end and a distal end; the proximal end of the retention member defining a seat for the connection member, the retention member being received in the first passage and movable relative to the anchor body, in the proximal-distal direction along the central longitudinal axis, from a retracted position where the proximal end of the retention member protrudes out of the proximal opening of the first passage, to a protracted position where the distal end protrudes out of the distal opening of the first passage and into the slot, wherein the distal end of the retention member includes an integrated serrated circular edge defining teeth positioned around the circumference forming a crown-shape, wherein the retention member includes a distal shank surmounted by a proximal enlarged head, and wherein the first passage has a cross-section configured to accommodate the shank, the head having a cross-section being larger than the cross-section of the first passage so that the head abuts on the distal wall when the retention member is moved towards the hook; and
   a connection member fastenable to the anchor body.

11. The stabilization system of claim 10, wherein the connection member is a rod positionable in the seat of the retention member.

12. The stabilization system of claim 10, wherein the anchor body includes a main passage extending essentially transverse to the proximal-distal direction and configured to receive a portion of the connection member, and wherein the proximal end of the retention member protrudes into the main passage in the protracted position.

13. The stabilization system of claim 12, wherein the fastening system includes a locking member for engagement with the anchor body, the locking member engaging with the anchor body and being displaceable so as to push the portion of the connection member towards the hook, thereby clamping the connection member inside the main passage.

14. The stabilization system of claim 10, wherein the retention member is freely movable in the distal-proximal direction relative to the anchor body.

\* \* \* \* \*